(12) United States Patent
Hirata et al.

(10) Patent No.: US 11,419,982 B2
(45) Date of Patent: Aug. 23, 2022

(54) DRIPPING DETECTION APPARATUS

(71) Applicant: Murata Manufacturing Co., Ltd., Kyoto (JP)

(72) Inventors: Atsuhiko Hirata, Kyoto (JP); Nobuhiro Kondo, Kyoto (JP); Kouji Miyabayashi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 591 days.

(21) Appl. No.: 15/913,170

(22) Filed: Mar. 6, 2018

(65) Prior Publication Data

US 2018/0193559 A1 Jul. 12, 2018

Related U.S. Application Data

(63) Continuation of application No. PCT/JP2016/076596, filed on Sep. 9, 2016.

(30) Foreign Application Priority Data

Sep. 9, 2015 (JP) .............................. JP2015-177588

(51) Int. Cl.
*A61M 5/168* (2006.01)
*G01F 1/661* (2022.01)
(Continued)

(52) U.S. Cl.
CPC ............ *A61M 5/1689* (2013.01); *G01F 1/661* (2013.01); *G01F 1/72* (2013.01); *G01F 23/292* (2013.01); *A61M 2205/3306* (2013.01)

(58) Field of Classification Search
CPC ......... A61M 5/1689; A61M 2205/3306; G01F 1/661; G01F 1/72; G01F 23/292
See application file for complete search history.

(56) References Cited

U.S. PATENT DOCUMENTS 4,038,981 A * 8/1977 LeFevre ............... A61M 5/1411
604/65
4,314,484 A * 2/1982 Bowman ................... G01F 3/00
128/DIG. 13
(Continued)

FOREIGN PATENT DOCUMENTS

CN 101920051 A 12/2010
JP 2008-528962 A 7/2008
(Continued)

OTHER PUBLICATIONS

JP 2014-204897 with translation from Espacenet (Year: 2014).*
(Continued)

*Primary Examiner* — Dung T Ulsh
(74) *Attorney, Agent, or Firm* — Pearne & Gordon LLP

(57) ABSTRACT

A dripping detection apparatus includes a cylindrical drip cylinder into which a nozzle is inserted from an upper side and that receives inside a liquid droplet dripping from a lower end of the nozzle, and a photo interrupter that has equal to or more than one light emitting element emitting light and equal to or more than two light receiving elements receiving the light, wherein the equal to or more than one light emitting element and the equal to or more than two light receiving elements are arranged at opposing or substantially opposing positions with the drip cylinder interposed between the elements and equal to or more than two light paths connecting the equal to or more than one light emitting element to the equal to or more than two light receiving elements are located at a lower side relative to the lower end of the nozzle.

11 Claims, 14 Drawing Sheets

(51) Int. Cl.
 *G01F 1/72* (2006.01)
 *G01F 23/292* (2006.01)

(56) References Cited

U.S. PATENT DOCUMENTS

| | | | | |
|---|---|---|---|---|
| 4,328,801 A * | 5/1982 | Marx | .................. | A61M 5/1689 |
| | | | | 604/253 |
| 5,588,963 A * | 12/1996 | Roelofs | ............... | A61M 5/1689 |
| | | | | 604/65 |
| 6,159,186 A | 12/2000 | Wickham et al. | | |
| 2008/0236580 A1 * | 10/2008 | Shang | ................. | A61M 16/183 |
| | | | | 128/203.16 |
| 2009/0044637 A1 | 2/2009 | Paz | | |
| 2010/0134303 A1 * | 6/2010 | Perkins | ............... | A61M 5/1684 |
| | | | | 340/619 |
| 2011/0046899 A1 * | 2/2011 | Paz | .................... | A61M 5/1689 |
| | | | | 702/46 |
| 2013/0188040 A1 * | 7/2013 | Kamen | ..................... | G01F 1/00 |
| | | | | 348/135 |
| 2013/0201482 A1 * | 8/2013 | Munro | .................... | G01N 21/27 |
| | | | | 356/407 |
| 2014/0267709 A1 * | 9/2014 | Hammond | ............. | G01N 21/85 |
| | | | | 348/143 |
| 2014/0276457 A1 * | 9/2014 | Munro | ................. | A61M 5/1411 |
| | | | | 604/251 |
| 2017/0156540 A1 * | 6/2017 | Wheatley | ............. | B67D 1/1238 |

FOREIGN PATENT DOCUMENTS

| | | |
|---|---|---|
| JP | 2012-125450 A | 7/2012 |
| JP | 2014-204897 A | 10/2014 |
| WO | 2014/160058 A2 | 10/2014 |

OTHER PUBLICATIONS

International Search Report for International Application No. PCT/JP2016/076596 dated Nov. 1, 2016.
Written Opinion of the International Search Report for International Application No. PCT/JP2016/076596 dated Nov. 1, 2016.

\* cited by examiner

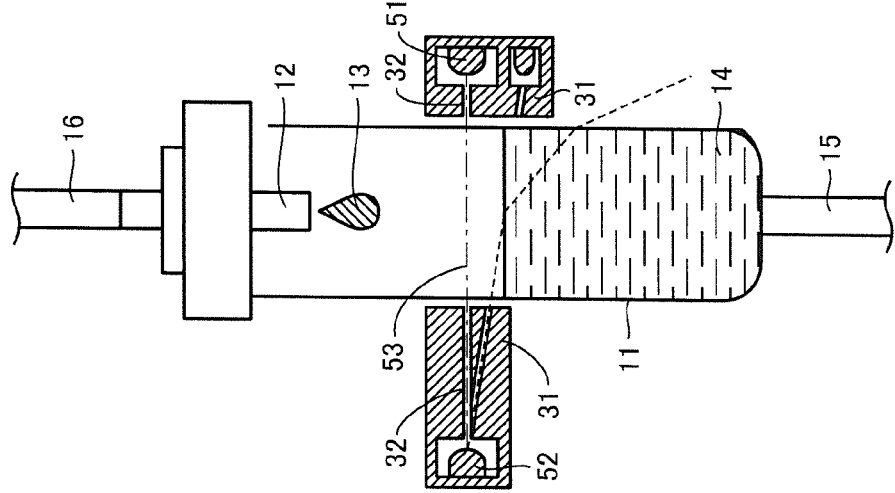
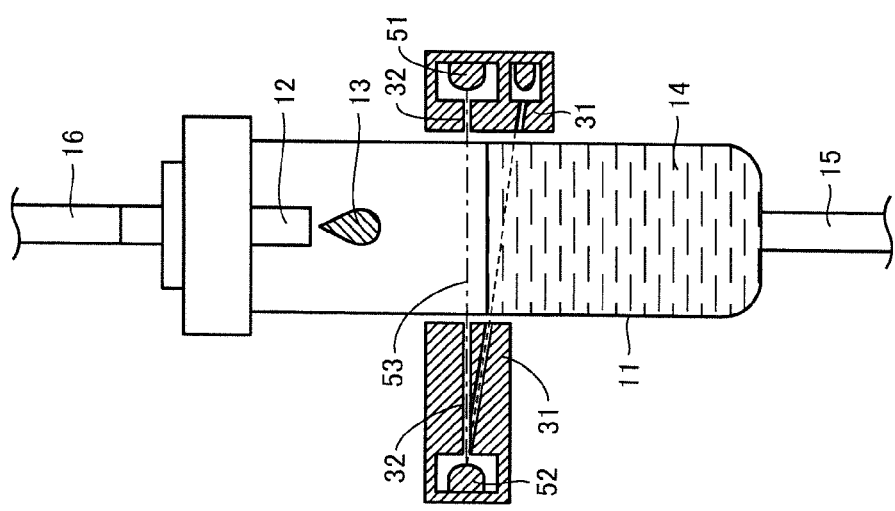

DRIPPING DETECTION APPARATUS

This is a continuation of International Application No. PCT/JP2016/076596 filed on Sep. 9, 2016 which claims priority from Japanese Patent Application No. 2015-177588 filed on Sep. 9, 2015. The contents of these applications are incorporated herein by reference in their entireties.

BACKGROUND OF THE DISCLOSURE

Field of the Disclosure

The present disclosure relates to a dripping detection apparatus.

Description of the Related Art

An existing transfusion system that counts the number of the liquid droplets dripping from the lower end of a nozzle in a drip cylinder and controls a dripping rate of the liquid droplets in accordance with the counted number have been known. For example, Japanese Unexamined Patent Application Publication No. 2012-125450 (Patent Document 1) discloses a drip infusion monitor device that detects the liquid droplets dripping in a light-transmissive drip cylinder by a light emitting element and a light receiving element and calculates the number of times of dripping and a dripping interval.

In the drip infusion monitor device disclosed in Patent Document 1, the light emitting element and the light receiving element are vertically arranged on one side surface of the drip cylinder, light having an orientation angle is outputted from the light emitting element to expose the liquid droplets in the drip cylinder thereto, and the light receiving element detects the reflected scattered light to grasp the dripping of the liquid droplets. With this configuration, the dripping of the liquid droplets can be grasped even when the drip cylinder is inclined with the motion of a patient, or the like, and the liquid droplets are missed without being exposed by the light traveling straight from the light emitting element. Therefore, a disadvantage that is generated when the light emitting element and the light receiving element are arranged in an opposing manner is eliminated.

Patent Document 1: Japanese Unexamined Patent Application Publication No. 2012-125450

BRIEF SUMMARY OF THE DISCLOSURE

However, in the drip infusion monitor device disclosed in Patent Document 1, since the light receiving element detects the scattered light, the detection sensitivity is therefore low.

Accordingly, it is desired that a dripping detection unit employing a mechanism of a photo interrupter while arranging a light emitting element and a light receiving element in an opposing manner is provided. In addition, the dripping detection unit capable of precisely grasping the dripping of the liquid droplets even when a drip cylinder is inclined with the motion of a patient, or the like, and the liquid droplets deviate without being exposed to the light traveling straight from the light emitting element is required to be realized.

The present disclosure has been made in view of the above-mentioned circumstances and an object thereof is to provide a dripping detection apparatus capable of precisely detecting the dripping even when a drip cylinder is inclined with the motion of a patient, or the like, and a liquid droplet deviates without being exposed to the light traveling straight from a light emitting element.

The present disclosure has the following characteristics in order to achieve the above-described object.

[1]

A dripping detection apparatus includes a cylindrical drip cylinder into which a nozzle is inserted from an upper side and that receives inside a liquid droplet dripping from a lower end of the nozzle, and a photo interrupter that has equal to or more than one light emitting element emitting light and equal to or more than two light receiving elements receiving the light, wherein the equal to or more than one light emitting element and the equal to or more than two light receiving elements are arranged at opposing or substantially opposing positions with the drip cylinder interposed between the elements, and equal to or more than two light paths connecting the equal to or more than one light emitting element to the equal to or more than two light receiving elements are located at a lower side relative to the lower end of the nozzle.

[2]

In the dripping detection apparatus according to [1], at least one of the equal to or more than two light paths toward the light receiving elements is non-parallel with the other light path when seen from above.

[3]

In the dripping detection apparatus according to [1] or [2], at least one of the equal to or more than two light paths toward the light receiving elements is non-parallel with the other light path when seen from a front side.

[4]

The dripping detection apparatus according to any one of [1] to [3] includes one light emitting element.

[5]

In the dripping detection apparatus according to [4], the drip cylinder is arranged between the light emitting element and the light receiving elements at a side closer to the light receiving elements.

[6]

In the dripping detection apparatus according to any one of [1] to [5], at least one of the equal to or more than two light paths intersects with the liquid droplet growing on the lower end of the nozzle.

[7]

In the dripping detection apparatus according to any one of [1] to [6], at least one of the equal to or more than two light paths is used for detecting a liquid level of a liquid reservoir in the drip cylinder.

[8]

The dripping detection apparatus according to any one of [1] to [7] includes an image capturing unit that captures the liquid droplet growing on the lower end of the nozzle and an illumination unit that is arranged at a position opposing or substantially opposing the image capturing unit with the drip cylinder interposed between the illumination unit and the image capturing unit, wherein the image capturing unit and the light receiving elements are arranged at opposing or substantially opposing positions with the drip cylinder between the image capturing unit and the light receiving elements.

According to the present disclosure, the dripping of a liquid droplet can be reliably detected by a photo interrupter which has equal to or more than one light emitting element and equal to or more than two light receiving elements and in which they are arranged at opposing or substantially opposing positions with a drip cylinder interposed between the elements.

BRIEF DESCRIPTION OF THE SEVERAL VIEWS OF THE DRAWINGS

FIGS. 15A, 15B and 15C are partially cross-sectional views for schematically explaining an effect that is provided by the dripping detection apparatus in the thirteenth embodiment.

DETAILED DESCRIPTION OF THE DISCLOSURE

Figure 1A:
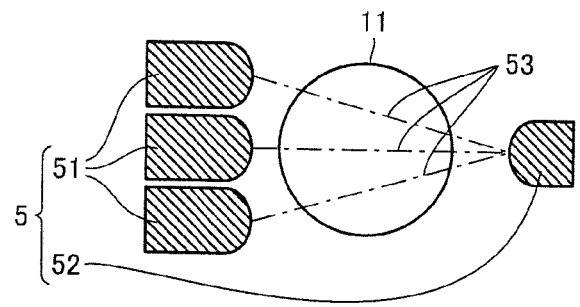
FIG. 1A is a schematic plan view schematically illustrating the schematic configuration of a dripping detection apparatus according to a first embodiment in a state in which a nozzle has been detached while omitting the illustration of a liquid reservoir.

Hereinafter, several embodiments according to the present disclosure will be described with reference to the drawings. In the drawings, the same reference numerals denote the same portions or corresponding portions. Furthermore, dimensional relations of a length, a width, a thickness, a depth, and the like are appropriately changed for clarifying and simplifying the drawings and do not indicate actual dimensional relations.

The respective embodiments are exemplary and partial replacement or combination of components in different embodiments can be made. The same action effects with the same configurations are not referred in each embodiment.

First Embodiment

<Dripping Detection Apparatus>

Figure 1B:
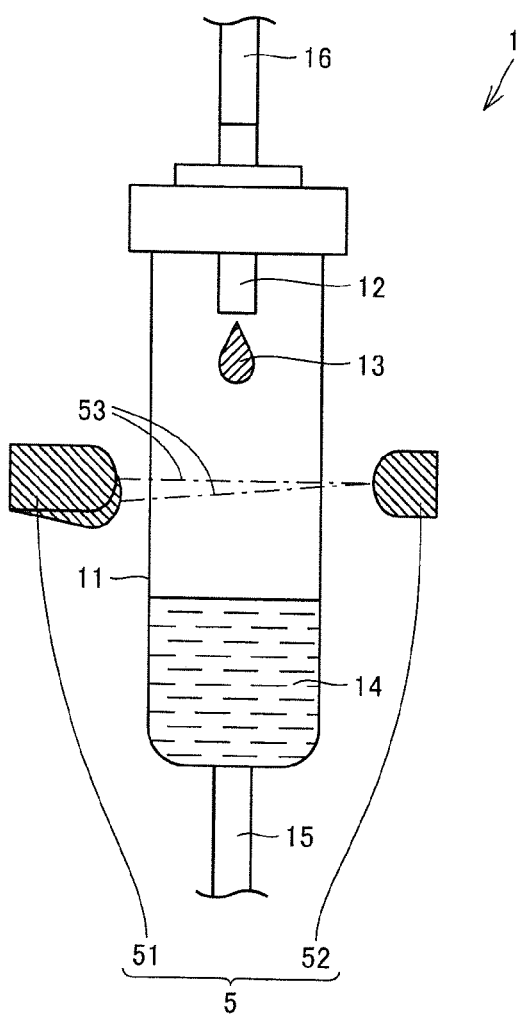
FIG. 1B is a schematic front view schematically illustrating the schematic configuration of the dripping detection apparatus in the first embodiment.

As illustrated in FIG. 1A and FIG. 1B, a dripping detection apparatus 1 according to a first embodiment includes a cylindrical drip cylinder 11 into which a nozzle 12 is inserted from the upper side and that receives inside a liquid droplet 13 dripping from the lower end of the nozzle 12, and a photo interrupter 5 that has equal to or more than one light emitting element 52 emitting light and equal to or more than two light receiving elements 51 receiving the light. The dripping detection apparatus 1 further includes a tube 15 for discharging the liquid droplet 13 that has dripped into the drip cylinder 11 from the drip cylinder 11.

<Drip Cylinder>

The drip cylinder 11 is arranged, for example, at a halfway position of a transfusion line reaching the human body from a transfusion bag hung on a stand at a higher position than the human body. The upper end of the nozzle 12 is connected to a tube 16 configuring the transfusion line at the transfusion bag side. An inner portion of the nozzle 12 communicates with an inner portion of the drip cylinder 11. In general, a liquid reservoir 14 storing therein a transfusion solution (drug solution) is formed in a lower portion of the drip cylinder 11. The lower end of the drip cylinder 11 is connected to the tube 15 configuring the transfusion line at the human body side.

The transfusion solution in the transfusion bag flows downward in the tube 16 with a gravity force and reaches the inner portion of the nozzle 12. The liquid droplet 13 of the transfusion solution grows on the lower end of the nozzle 12 and drips into the drip cylinder 11 when the liquid droplet 13 becomes a predetermined size. The drip cylinder 11 allows visible light and infrared light to pass therethrough and the growing liquid droplet 13 can therefore be checked visually from the outside. The drip cylinder 11 does not also shield infrared light from an infrared LED (light emitting diode).

<Photo Interrupter>

The photo interrupter 5 has equal to or more than one light emitting element 52 emitting light and equal to or more than two light receiving elements 51 receiving the light. The equal to or more than one light emitting element 52 and the equal to or more than two light receiving elements 51 are arranged at opposing or substantially opposing positions with the drip cylinder 11 interposed therebetween. Furthermore, equal to or more than two light paths 53 connecting the equal to or more than one light emitting element 52 to the equal to or more than two light receiving elements 51 are located at the lower side relative to the lower end of the nozzle 12.

The light emitting element 52 is, for example, a light emitting diode, and has a light emitting portion and emits light toward the dripping liquid droplet 13 (and the light receiving elements 51) from the light emitting portion. The light receiving elements 51 are, for example, photo transistors, and have light receiving portions. The light receiving portions detect whether or not the light emitted from the light emitting element 52 is shielded by the dripping liquid droplet 13. The light receiving elements 51 may have the configuration in which the light receiving portions detect the variation in the amount of the light emitted from the light emitting element 52 by passing through the dripping liquid droplet.

A light source of the light emitting element 52 is not particularly limited and examples thereof can include an infrared LED, a visible light laser, and the like. When the infrared LED is used, flashing or lighting of the light emitting element 52 is not annoying even when a patient is subject to drip infusion in the nighttime or the like.

The photo interrupter 5 can detect the occurrence of dripping (the separation of the liquid droplet 13 from the lower end of the nozzle 12) and count the number of times of dripping based on the detection of light shielding or the variation in the amount of light by the light receiving portions of the light receiving elements 51.

The light paths 53 in the specification are, to be specific, light passages connecting the light emitting portion of the light emitting element 52 to the light receiving portions of the light receiving elements 51. The light emitted from the light emitting element 52 spreads as it travels but only light components of the light, which connect the light emitting portion of the light emitting element 52 and the light receiving portions of the light receiving elements 51, form the light paths 53. The dashed-dotted lines in the accompany drawings of the present application indicate the light paths 53. It should be noted that the solid lines indicate the light paths 53 in FIG. 8.

In the specification, when the light path 53 connecting the certain light emitting element 52 to the certain light receiving element 51 have such relation that passes through the inner portion of the drip cylinder 11, it is expressed that the light emitting element 52 and the light receiving element 51 are arranged at "substantially opposing" positions with the drip cylinder 11 interposed therebetween. In particular, when the certain light emitting element 52 and the certain light receiving element 51 are located at positions so as to face each other with the drip cylinder 11 interposed therebetween, it is expressed that the light emitting element 52 and the light receiving element 51 are arranged at "opposing" positions with the drip cylinder 11 interposed therebetween.

The dripping detection apparatus 1 in the first embodiment includes the equal to or more than two light receiving elements 51. To be specific, as illustrated in FIG. 1A, the dripping detection apparatus 1 includes three light receiving elements 51. At least one of the light paths 53 toward the respective light receiving elements 51 is non-parallel with the other light paths 53 when seen from the above. As illustrated in FIG. 1B, at least one of the light paths 53 toward the respective light receiving elements 51 is also non-parallel with the other light paths 53 when seen from the front side. In the embodiment, one light emitting element 52 is provided.

Furthermore, a depression angle or an elevation angle is given to one light receiving element 51 of the three light receiving elements 51 arranged at positions opposing or substantially opposing the light emitting element 52 with the drip cylinder 11 interposed therebetween. To be specific, as illustrated in FIG. 1B, the depression angle is given to the light receiving element 51 at the center, which opposes the light emitting element 52 with the drip cylinder 11 interposed therebetween, among the three light receiving elements 51 aligned with the same orientation in a row in the depth direction. The one light emitting element 52 and the light receiving portions of the light receiving elements 51 at both ends among the three light receiving elements 51 are arranged on the same plane.

With this arrangement, the respective light paths 53 toward the light receiving elements 51 at both ends among the three light receiving elements 51 extend horizontally when seen from the front side. On the other hand, the light path 53 toward the light receiving element 51 at the center, which has the given depression angle, does not extend horizontally but is inclined when seen from the front side and forms non-parallel relations with the other two light paths 53 when seen from the front side. Furthermore, the depression angle is given to the light receiving element 51 at the center and the light receiving portion thereof does not therefore face at right the light emitting portion of the light emitting element 52. What the light emitting portion of the light emitting element 52 "faces at right" indicates that an angle formed by the light path 53 and the surface of the light emitting portion is a right angle. What the light receiving portion of the light receiving element 51 "faces at right" indicates that an angle formed by the light path 53 and the surface of the light receiving portion is a right angle.

As illustrated in FIG. 1A, the light path 53 toward the light receiving element 51 at the center among the three light receiving elements 51 extends to right and left straightly when seen from the above. On the other hand, the light paths 53 toward the light receiving elements 51 at both ends extend to right and left while being inclined when seen from the above and form non-parallel relations with the light path 53 toward the light receiving element 51 at the center when seen from the above. The respective light receiving elements 51 at both ends are also substantially oppose the light emitting element 52 with the drip cylinder 11 interposed therebetween but do not strictly oppose it. Therefore, the light receiving portions thereof do not face at right the light emitting portion of the light emitting element 52. In summary, in the embodiment, none of the light receiving portions of the three light receiving elements 51 faces at right the light emitting portion of the light emitting element 52.

When the depression angle or the elevation angle is not added to the light receiving element at the center among the three light receiving elements aligned with the same orientation in a row in the depth direction, the light receiving element at the center opposes and faces at right the light emitting element. In this case, when the amount of light which is received by the light receiving portion of the light receiving element at the center becomes excess and is saturated, there may be a case in which the light receiving element becomes incapable of recognizing the shielding of the light emitted from the light emitting element even if the liquid droplet intersects with the light path and cannot detect the dripping thereof. Furthermore, when the amount of light of the light emitting element is reduced so as to prevent the amount of light which is received by the light receiving portion of the light receiving element at the center from being saturated in consideration of the above-described case, the amount of light which is received by each of the light receiving portions of the light emitting elements at both ends is excessively small. In this case, there may be a case in which the light receiving elements at both ends recognize that the light emitted from the light emitting element is shielded by the liquid droplet all the time and the dripping of the liquid droplet cannot be precisely detected.

The amount of light which is received by each of the light emitting elements at both ends is also excessively small even when the light emitting element is not arranged on the same plane as the light receiving elements as described above but arranged to deviate therefrom in height and the amount of light which is received by the light receiving element at the center is adjusted so as not to be saturated. Therefore, also in this case, there may be a case in which the dripping of the liquid droplet cannot be accurately detected.

For avoiding these cases, in the embodiment, the light receiving elements 51 and the light emitting element 52 are arranged so as not to have a relation of facing at right each other based on the above-described configuration and the depression angle which is added to the light receiving element 51 at the center is adjusted. In this manner, the three light receiving elements 51 are made to be capable of receiving substantially the same amounts of light from the light emitting element 52. That is to say, the light receiving element 51 at the center can receive substantially the same amount of light as the amount of light which is received by each of the light receiving elements 51 at both ends by adjusting the angle of the depression angle which is added thereto. Furthermore, all of the light receiving elements 51 can receive the appropriate amounts of light by adjusting the light amount of the light emitting element 52. Accordingly, the light receiving elements 51 at all of the positions regardless of the center or both ends can detect the dripping of the liquid droplet 13.

In the embodiment, the light paths 53 toward the light receiving elements 51 pass through different positions in the horizontal direction and the vertical direction in the drip cylinder 11 with the above-described configuration. Accordingly, even when a dripping path of the liquid droplet 13 in the drip cylinder 11 deviates from an extended line from the lower end of the nozzle 12 due to the inclination or vibration, the liquid droplet 13 intersects with any of the light paths 53 and the dripping thereof can be precisely detected. Moreover, in the embodiment, the dripping of the liquid droplet 13 can be reliably detected because the light emitting element 52 and the light receiving elements 51 are arranged at the opposing or substantially opposing positions with the drip cylinder 11 interposed therebetween.

In the dripping detection apparatus 1, the amount of light that passes through the drip cylinder 11 from the light emitting element 52 and is received by each of the light receiving elements 51 not only varies by light shielding and refraction by the dropping liquid droplet but also largely varies by the interference between the liquid droplets which have adhered to the inner wall of the drip cylinder 11 and each of the light paths 53. The amount of light which is received by each of the light receiving elements 51 also largely varies due to the variation in the light amount of sun light reaching each of the light receiving elements, which is caused by change in weather, change in sunshine with the passage of time, and brightness of a room, and the like. In consideration of this situation, in the embodiment, a determination unit detecting a dropping liquid droplet (also referred to as "drop") determines the detection of the drop not based on whether or not the output voltages of the light receiving elements 51 are equal to or higher than a single threshold value but when the voltage value is largely lowered instantaneously relative to an average value of the latest output voltages of the light receiving elements 51.

This configuration can be realized by, for example, converting the output voltages of the equal to or more than two light receiving elements into pieces of digital data by an A-to-D converter and taking the pieces of digital data into a calculation unit for calculation. The above-described configuration can also be realized by an analog circuit. For example, the detection of the drop can be determined (a light shielding state and a light transmitting state can be judged) by averaging the output voltages of the equal to or more than two light receiving elements in terms of time by a low pass filter, outputting a difference between the averaged voltage value and a current voltage value by a subtraction circuit, and comparing the output value and a predetermined threshold value using a comparator. Therefore, accurate drop detection determination can also be realized by the analog circuit by taking the determined or judged data into a controller by digital I/O (input/output).

Furthermore, in the embodiment, at least one of the equal to or more than two light paths 53 can be used for detecting the liquid level of the liquid reservoir 14 in the drip cylinder 11. That is to say, as will be described in detail later in a thirteenth embodiment, the liquid level of the liquid reservoir 14 is recognized to be abnormal when the light receiving portion of the light receiving element 51 detects the light shielding or the variation in the light amount over a predetermined period of time or through a predetermined period of time. The light paths 53 can thereby be made to have the function of detecting the dripping of the liquid droplet 13 and a function as a liquid level sensor detecting that the liquid level of the liquid reservoir 14 reaches to the light path 53 or has a risk of reaching it.

Hydrophilic treatment is performed on the inner wall surface of the drip cylinder 11 as an example of a method for avoiding the large variation in the amount of light which is received by each of the light receiving elements 51 due to the interference between the liquid droplets which have adhered to the inner wall surface of the drip cylinder 11 and each of the light paths 53 as described above. In this case, the liquid droplets which have adhered to the inner wall surface spread with small contact angles and do not therefore remain as droplets on the inner wall surface of the drip cylinder 11. For this reason, the hydrophilic treatment is preferable.

Second Embodiment

Figure 2A:
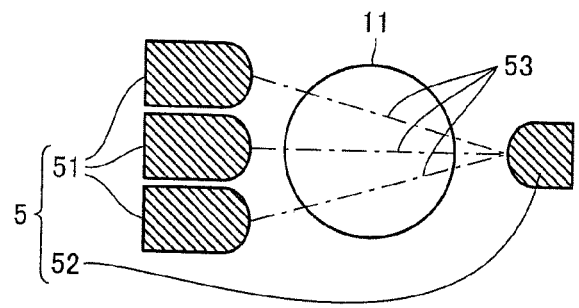
FIG. 2A is a schematic plan view schematically illustrating the schematic configuration of a dripping detection apparatus according to a second embodiment in a state in which a nozzle has been detached while omitting the illustration of a liquid reservoir.
Figure 2B:
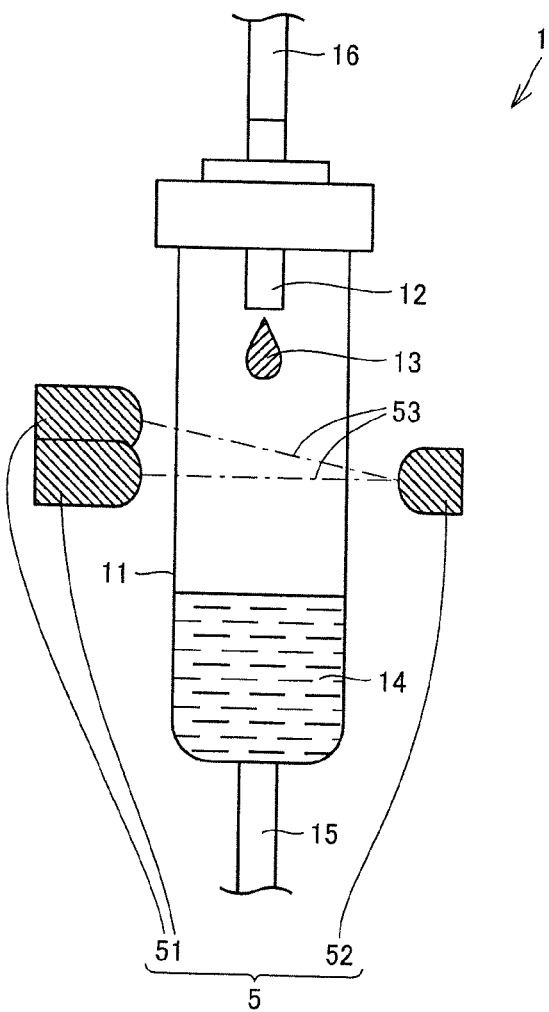
FIG. 2B is a schematic front view schematically illustrating the schematic configuration of the dripping detection apparatus in the second embodiment.

The dripping detection apparatus 1 according to a second embodiment is different from the first embodiment in the following point. That is, the height at which the light receiving element 51 at the center among the three light receiving elements 51 is arranged when seen from the front side and each of the heights at which the light receiving elements 51 at both ends are arranged when seen from the front side are different from each other, as illustrated in FIG. 2A and FIG. 2B. To be specific, the height of the light receiving element 51 at the center when seen from the front side is larger than each of the heights of the light receiving elements 51 at both ends when seen from the front side. Furthermore, the dripping detection apparatus 1 in the second embodiment is different from the first embodiment also in a point that neither the depression angle nor the elevation angle is given to the light receiving element 51 at the center. Other configurations are the same as those in the first embodiment.

In the embodiment, as illustrated in FIG. 2B, the respective light paths 53 toward the light receiving elements 51 at both ends among the three light receiving elements 51 extend horizontally when seen from the front side. On the other hand, the light path 53 toward the light receiving element 51 at the center does not extend horizontally but is inclined when seen from the front side and forms non-parallel relations with the light paths 53 toward the light receiving elements 51 at both ends when seen from the front side. Furthermore, the light receiving portion of the light receiving element 51 at the center does not face at right the light emitting portion of the light emitting element 52 because each of the heights thereof is different from that of the light emitting element 52 when seen from the front side.

As illustrated in FIG. 2A, the light path 53 toward the light receiving element 51 at the center among the three light receiving elements 51 extends to right and left straightly when seen from the above. On the other hand, the light paths 53 toward the light receiving elements 51 at both ends extend to right and left while being inclined when seen from the above and form non-parallel relations with the light path 53 toward the light receiving element 51 at the center when seen from the above. The respective light receiving elements 51 at both ends also substantially oppose the light emitting element 52 with the drip cylinder 11 interposed therebetween but do not strictly oppose it. Therefore, the light receiving portions thereof do not face at right the light emitting portion of the light emitting element 52. In summary, also in the embodiment, all of the light receiving portions of the three light receiving elements 51 do not face at right the light emitting portion of the light emitting element 52.

Accordingly, the embodiment also enables the light receiving portions of all of the light receiving elements 51 to receive substantially the same amounts of light from the light emitting element 52 by adjusting the height of the light receiving element 51 at the center when seen from the front side. Therefore, all of the light receiving elements 51 can receive the appropriate amounts of light by adjusting the light amount of the light emitting element 52. Thus, the light receiving elements 51 at all of the positions regardless of the center or both ends can detect the dripping of the liquid droplet 13. Furthermore, the light paths 53 toward the respective light receiving elements 51 pass through different positions in the horizontal direction and the vertical direction in the drip cylinder 11. Therefore, the liquid droplet 13 necessarily intersects with any of the light paths 53 and the dripping thereof can be precisely detected. Moreover, the light emitting element 52 and the light receiving elements 51 are arranged at the opposing or substantially opposing positions with the drip cylinder 11 interposed therebetween, so that the dripping of the liquid droplet 13 can be reliably detected.

Third Embodiment

Figure 3A:
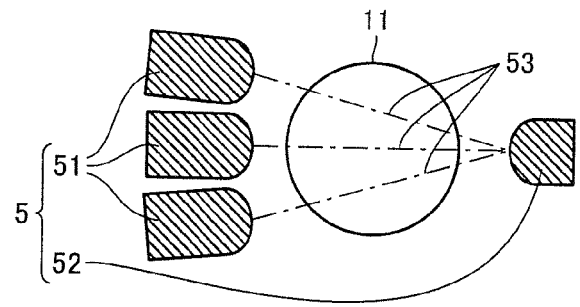
FIG. 3A is a schematic plan view schematically illustrating the schematic configuration of a dripping detection apparatus according to a third embodiment in a state in which a nozzle has been detached while omitting the illustration of a liquid reservoir.

The dripping detection apparatus 1 according to a third embodiment is different from the first embodiment in the following point. That is, the light receiving portions of the light receiving elements 51 at both ends among the three light receiving elements 51 are arranged to direct slightly inward to the direction of making close to the light emitting portion of the light emitting element 52 so that they substantially oppose with the drip cylinder 11 interposed therebetween, as illustrated in FIG. 3A. It should be noted that the light receiving portions of the light receiving elements 51 at both ends do not face at right the light emitting element 52. In the third embodiment, the depression angle or the elevation angle is given to the light receiving element 51 at the center in the same manner as the first embodiment. Other configurations in the third embodiment are the same as those in the first embodiment.

Figure 3B:
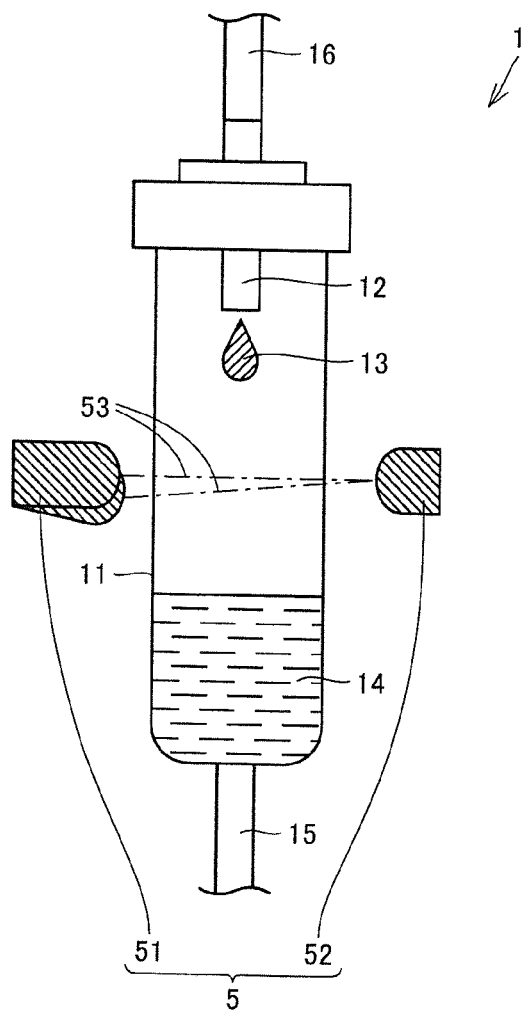
FIG. 3B is a schematic front view schematically illustrating the schematic configuration of the dripping detection apparatus in the third embodiment.

In the embodiment, as illustrated in FIG. 3B, the respective light paths 53 toward the light receiving elements 51 at both ends among the three light receiving elements 51 extend horizontally when seen from the front side. On the other hand, the light path 53 toward the light receiving element 51 at the center, which has the given depression angle, does not extend horizontally but is inclined when seen from the front side and forms non-parallel relations with the light paths 53 toward the light receiving elements 51 at both ends when seen from the front side. Furthermore, the depression angle is given to the light receiving element 51 at the center and the light receiving portion thereof does not therefore face at right the light emitting portion of the light emitting element 52.

As illustrated in FIG. 3A, the light path 53 toward the light receiving element 51 at the center among the three light receiving elements 51 extends to right and left straightly when seen from the above. On the other hand, the light paths 53 toward the light receiving elements 51 at both ends extend to right and left while being inclined when seen from the above and form non-parallel relations with the light path 53 toward the light receiving element 51 at the center when seen from the above. The respective light receiving elements 51 at both ends are substantially oppose the light emitting element 52 with the drip cylinder 11 interposed therebetween and direct to the direction of making close to the light emitting portion of the light emitting element 52 but the light receiving portions thereof do not face at right the light emitting portion of the light emitting element 52 as described above. In summary, also in the embodiment, all of the light receiving portions of the three light receiving elements 51 do not face at right the light emitting portion of the light emitting element 52.

Accordingly, the embodiment also enables the light receiving portions of all of the light receiving elements 51 to receive substantially the same amounts of light from the light emitting element 52 by adjusting the angle of the depression angle which is given to the light receiving element 51 at the center and adjusting an extent that the light receiving elements 51 at both ends are made to direct to the direction of making close to the light emitting portion of the light emitting element 52. Therefore, all of the light receiving elements 51 can receive the appropriate amounts of light by adjusting the light amount of the light emitting element 52. Thus, the light receiving elements 51 at all of the positions regardless of the center or both ends can detect the dripping of the liquid droplet 13. Furthermore, the light paths 53 toward the respective light receiving elements 51 pass through different positions in the horizontal direction and the vertical direction in the drip cylinder 11. Therefore, the liquid droplet 13 necessarily intersects with any of the light paths 53 and the dripping thereof can be precisely detected. Moreover, the light emitting element 52 and the light receiving elements 51 are arranged at the opposing or substantially opposing positions with the drip cylinder 11 interposed therebetween, so that the dripping of the liquid droplet 13 can be reliably detected.

In particular, the embodiment can make the amounts of light which is received by the respective light receiving elements 51 be extremely close to the same amount by adjusting the angle of the depression angle or the elevation angle which is given to the light receiving element 51 at the center and adjusting the extent that the light receiving elements 51 at both ends are made to direct to the direction of making close to the light emitting portion of the light emitting element 52. Therefore, the dripping of the liquid droplet 13 can be detected more precisely.

Although the first embodiment to the third embodiment illustrate the configuration in which the number of light receiving elements 51 is three as an example, the number of light receiving elements in the disclosure is not limited to three. That is to say, the number of light receiving elements can be appropriately determined as long as the plurality of light receiving elements can establish a relation capable of receiving substantially the same amounts of light from the equal to or more than one light emitting element. It should be noted that the number of light receiving elements is preferably equal to or more than three while considering the prevention of the dripping detection apparatus from being increased in size.

Fourth Embodiment

Figure 4A:
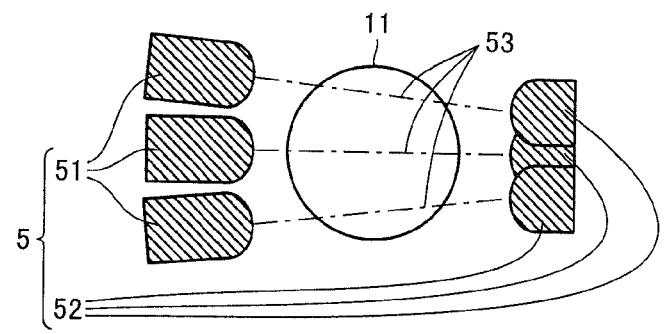
FIG. 4A is a schematic plan view schematically illustrating the schematic configuration of a dripping detection apparatus according to a fourth embodiment in a state in which a nozzle has been detached while omitting the illustration of a liquid reservoir.
Figure 4B:
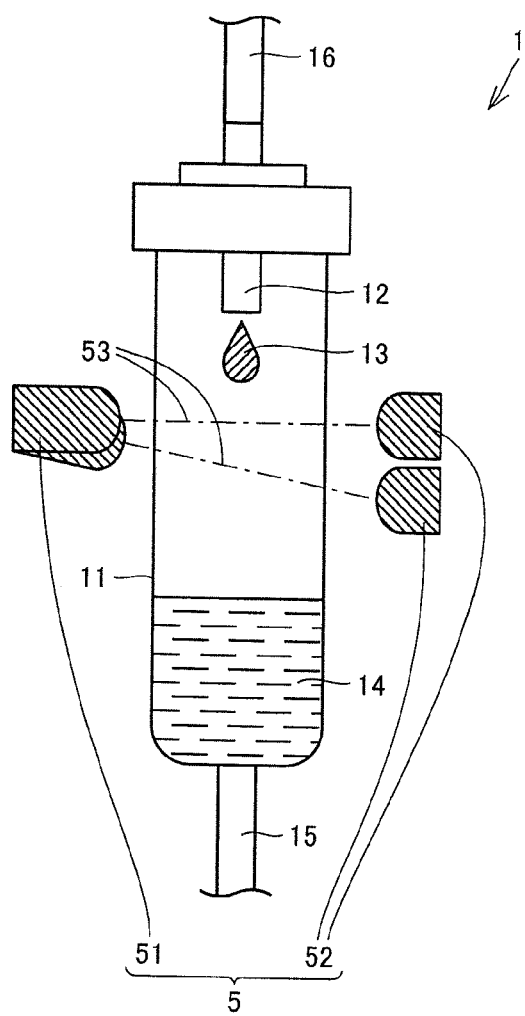
FIG. 4B is a schematic front view schematically illustrating the schematic configuration of the dripping detection apparatus in the fourth embodiment.

The dripping detection apparatus 1 according to a fourth embodiment is different from the first embodiment in a point that three light emitting elements 52 are arranged, as illustrated in FIG. 4A and FIG. 4B. Among the three light emitting elements 52, the height of the light emitting element 52 at the center when seen from the front side is different from each of the heights of the light emitting elements 52 at both ends when seen from the front side. To be specific, each of the heights of the light emitting elements 52 at both ends when seen from the front side is larger than the height of the light emitting element 52 at the center when seen from the front side. The dripping detection apparatus 1 in the fourth embodiment is different from the first embodiment also in a point that the light receiving elements 51 at both ends among the three light receiving elements 51 are arranged slightly inward so as to direct to the direction of making close to the light emitting portions of the light emitting elements 52 in the same manner as the third embodiment. It should be noted that the depression angle or the elevation angle is given to the light receiving element 51 at the center in the same manner as the first embodiment.

With the arrangement of the three light emitting elements 52 and the arrangement of the three light receiving elements 51 as described above, the light receiving portion of the light receiving element 51 at the center, which has the given depression angle, opposes the light emitting element 52 at the center with the drip cylinder 11 interposed therebetween and faces at right the light emitting portion thereof. The light receiving portions of the light receiving elements 51 at both ends respectively oppose the light emitting elements 52 at both ends with the drip cylinder 11 interposed therebetween and face at right the light emitting portions thereof. Furthermore, the three light emitting elements 52 are arranged so as to be close to each other in a crowded manner in comparison with the arrangement of the three light receiving elements 51. Other configurations are the same as those in the first embodiment.

In the embodiment, as illustrated in FIG. 4B, the respective light paths 53 toward the light receiving elements 51 at both ends among the three light receiving elements 51 extend horizontally when seen from the front side. On the other hand, the light path 53 toward the light receiving element 51 at the center, which has the given depression angle, does not extend horizontally but is inclined when seen from the front side and forms non-parallel relations with the light paths 53 toward the light receiving elements 51 at both ends when seen from the front side. As illustrated in FIG. 4A, the light path 53 toward the light receiving element 51 at the center among the three light receiving elements 51 extends to right and left straightly when seen from the above. On the other hand, the light paths 53 toward the light receiving elements 51 at both ends extend to right and left while being inclined when seen from the above and form non-parallel relations with the light path 53 toward the light receiving element 51 at the center when seen from the above.

The light receiving portions of the three light receiving elements 51 respectively face at right the light emitting portions of the three light emitting elements 52. Therefore, the light receiving portions of all of the light receiving elements 51 can receive substantially the same appropriate amounts of light by adjusting the amounts of light from the light emitting elements 52. Accordingly, the light receiving elements 51 at all of the positions regardless of the center or both ends can detect the dripping of the liquid droplet 13. Furthermore, the light paths 53 toward the respective light receiving elements 51 pass through different positions in the horizontal direction and the vertical direction in the drip cylinder 11. Therefore, the liquid droplet 13 necessarily intersects with any of the light paths 53 and the dripping thereof can be precisely detected. The light emitting elements 52 and the light receiving elements 51 are arranged at the opposing or substantially opposing positions with the drip cylinder 11 interposed therebetween, so that the dripping of the liquid droplet 13 can be reliably detected.

In particular, in the embodiment, the light receiving portions of the three light receiving elements 51 face at right the light emitting portions of the three light emitting elements 52. Therefore, the amounts of light which is received by the respective light receiving elements 51 can be made extremely close to the same amount by adjusting the amounts of light which is emitted from the respective light emitting elements 52, thereby detecting the dripping of the liquid droplet 13 more precisely. Furthermore, the three light emitting elements 52 are arranged so as to be close to one another in comparison with the arrangement of the three light receiving elements 51 as described above. This arrangement manner decreases the distances between the respective three light paths 53 connecting the three light emitting elements 52 to the three light receiving elements 51 when seen from the above, thereby preventing the occurrence of the case in which the liquid droplet 13 passes through between one of the light paths 53 and another one of the light paths 53.

Fifth Embodiment

Figure 5A:
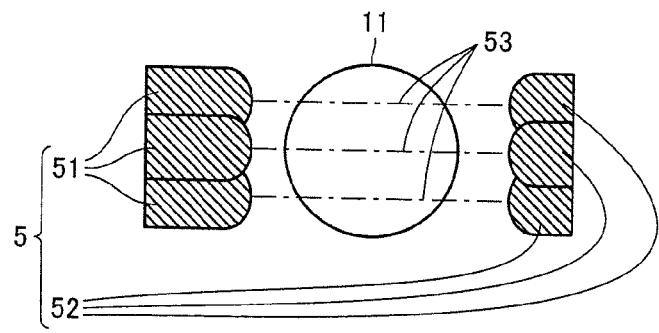
FIG. 5A is a schematic plan view schematically illustrating the schematic configuration of a dripping detection apparatus according to a fifth embodiment in a state in which a nozzle has been detached while omitting the illustration of a liquid reservoir.
Figure 5B:
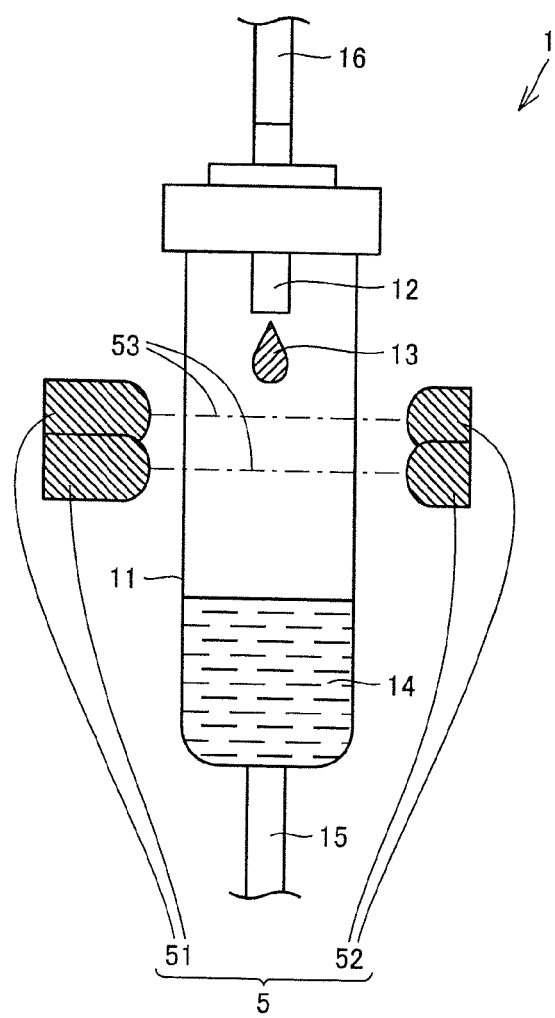
FIG. 5B is a schematic front view schematically illustrating the schematic configuration of the dripping detection apparatus in the fifth embodiment.

The dripping detection apparatus 1 according to a fifth embodiment is different from the first embodiment in a point that the three light emitting elements 52 are arranged in the same manner as the fourth embodiment, as illustrated in FIG. 5A and FIG. 5B. Furthermore, the height of the light emitting element 52 at the center when seen from the front side is different from each of the heights of the light emitting elements 52 at both ends when seen from the front side. To be specific, the height of the light emitting element 52 at the center when seen from the front side is larger than each of the heights of the light emitting elements 52 at both ends when seen from the front side. The three light emitting elements 52 direct to the same direction.

Furthermore, the fifth embodiment is different from the first embodiment in a point that the height of the light receiving element 51 at the center among the three light receiving elements 51 when seen from the front side is different from each of the heights of the light receiving elements 51 at both ends when seen from the front side. To be specific, the height of the light receiving element 51 at the center when seen from the front side is larger than each of the heights of the light receiving elements 51 at both ends when seen from the front side. The three light receiving elements 51 direct to the same direction. The three light receiving elements 51 and the three light emitting elements 52 are arranged so as to be close to one another in the same manner as the respective three light emitting elements 52 in the fourth embodiment. This arrangement manner decreases the distances between the three light paths 53 when seen from the above. It should be noted that other configurations are the same as those in the first embodiment.

With the arrangement of the three light emitting elements 52 and the arrangement of the three light receiving elements 51 as described above, the light emitting portion of the light emitting element 52 at the center opposes the light receiving element 51 at the center with the drip cylinder 11 interposed therebetween and faces at right the light receiving portion thereof. The respective light emitting portions of the light emitting elements 52 at both ends oppose the light receiving elements 51 at both ends with the drip cylinder 11 interposed therebetween and face at right the light receiving portions thereof. The light receiving portions of the three light receiving elements 51 respectively face at right the light emitting portions of the three light emitting elements 52. Therefore, the light receiving portions of all of the light receiving elements 51 can receive substantially the same appropriate amounts of light by adjusting the amounts of light from the light emitting elements 52.

Accordingly, also in the embodiment, the light receiving elements 51 at all of the positions regardless of the center or both ends can detect the dripping of the liquid droplet 13. Furthermore, the liquid droplet 13 necessarily intersects with any of the light paths 53 and the dripping thereof can be precisely detected. Moreover, the distances between the respective three light paths 53 connecting the three light emitting elements 52 to the three light receiving elements 51 are decreased when seen from the above, thereby preventing the occurrence of the case in which the liquid droplet 13 passes through between one of the light paths 53 and another one of the light paths 53. In addition, the light emitting elements 52 and the light receiving elements 51 are arranged at the opposing or substantially opposing positions with the drip cylinder 11 interposed therebetween, so that the dripping of the liquid droplet 13 can be reliably detected.

In the disclosure, the mode in which the three light receiving elements 51 and the three light emitting elements 52 are arranged is not limited to the modes described in the fourth embodiment and the fifth embodiment as the examples. An appropriate arrangement mode of the three light receiving elements 51 and the three light emitting elements 52 can be employed as long as the light receiving portions of three light receiving elements and the light emitting portions of the three light emitting elements can establish the relation of facing at right each other.

Sixth Embodiment

In a sixth embodiment, the preferable number of light emitting elements configuring a dripping detection apparatus is described.

Figure 6:
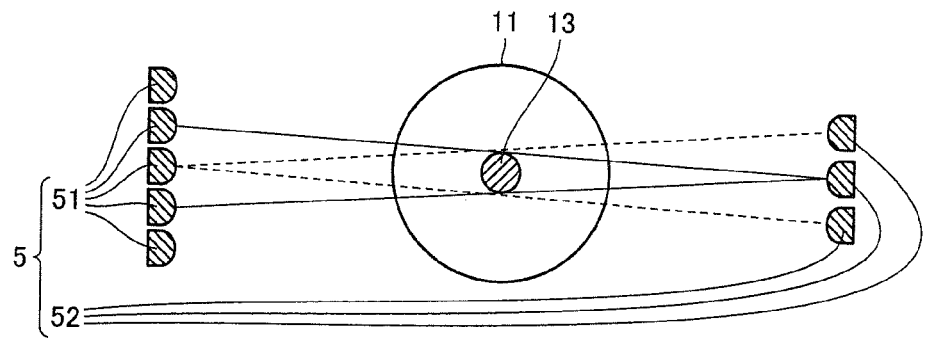
FIG. 6 is a partially cross-sectional descriptive view for schematically explaining an effect that is provided by a dripping detection apparatus according to a sixth embodiment.

The dripping detection apparatus in the sixth embodiment includes a cylindrical drip cylinder into which a nozzle is inserted from the upper side and that receives inside the liquid droplets dripping from the lower end of the nozzle, and a photo interrupter that has equal to or more than one light emitting element emitting light and equal to or more than one light receiving element receiving the light. As illustrated in FIG. 6, the dripping detection apparatus in the sixth embodiment includes the photo interrupter 5 formed by three light emitting elements 52 and five light receiving elements 51, and the light emitting elements 52 and the light receiving elements 51 are arranged at opposing or substantially opposing positions with the drip cylinder 11 interposed therebetween. The light paths 53 connecting the light emitting elements 52 to the light receiving elements 51 are located at the lower side relative to the lower end of the nozzle.

In particular, the five light receiving elements 51 are aligned with the same orientation in a row in the longitudinal direction on the same plane. The three light emitting elements 52 are also aligned with the same orientation in a row in the longitudinal direction on the same plane. The five light receiving elements 51 and the three light emitting elements 52 are present on the same plane in the sixth embodiment. In the disclosure, a positional relation between the light receiving elements and the light emitting elements may be such relation that they are present on the same plane or such relation that they are present with different heights as long as they are arranged at the opposing or substantially opposing positions with the drip cylinder interposed therebetween.

In this configuration, when only the light emitting element 52 at the center among the three light emitting elements 52 is made to emit light, the intersection between the light path 53 thereof and the liquid droplet 13 causes the shadows indicated by the solid lines in FIG. 6 to be projected onto the light receiving element 51 at the center among the five light receiving elements 51. The light receiving element 51 at the center recognizes that the liquid droplet 13 shields the light path 53 based on the shadows and detects the dripping of the liquid droplet 13. In this case, the light emitting elements 52 at both ends do not emit light and the shadows with high contrast are therefore obtained in the light receiving element 51 at the center.

On the other hand, when all of the three light emitting elements 52 are made to emit light, shadows are projected in a range as indicated by the solid lines in FIG. 6 and the light as indicated by the dashed lines in FIG. 6 reaches the light receiving element 51 at the center from the light emitting elements 52 at both ends. In summary, in a state in which the light receiving element 51 at the center tries to grasp the shielding of the light path 53 by the liquid droplet 13, each light from the light emitting elements 52 at both ends is incident and the shadows of the liquid droplet 13 with high contrast are not obtained in the light receiving element 51 at the center. When the high contrast is not obtained, there is a risk that the light receiving element 51 at the center cannot detect the dripping of the liquid droplet 13 in some cases.

Accordingly, the number of light emitting elements configuring the dripping detection apparatus is preferably one. Furthermore, the plurality of light receiving elements 51 reduced in size are preferably arranged so as to be close to each other. With this configuration, the liquid droplet 13 necessarily intersects with any of the light paths 53 passing through the inner portion of the drip cylinder 11 and the dripping of the liquid droplet 13 can therefore be precisely detected even when the drip cylinder 11 is inclined.

Seventh Embodiment

In a seventh embodiment, a preferable position at which a drip cylinder configuring a dripping detection apparatus is arranged is described.

Figure 7:
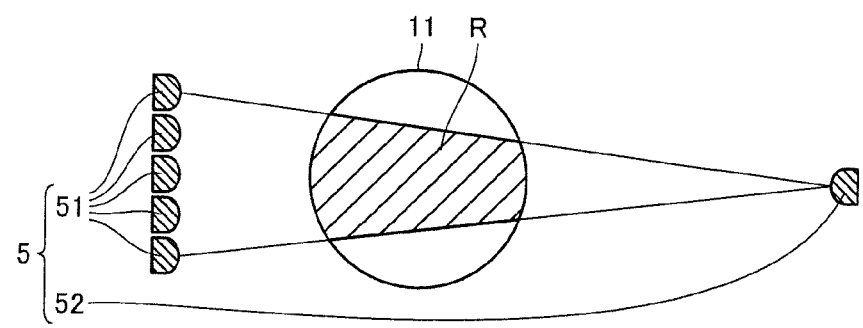
FIG. 7 is a partially cross-sectional descriptive view for schematically explaining an effect that is provided by a dripping detection apparatus according to a seventh embodiment.

The dripping detection apparatus in the seventh embodiment includes a cylindrical drip cylinder into which a nozzle is inserted from the upper side and that receives inside the liquid droplets dripping from the lower end of the nozzle, and a photo interrupter that has equal to or more than one light emitting element emitting light and equal to or more than one light receiving element receiving the light. As illustrated in FIG. 7, the dripping detection apparatus in the seventh embodiment includes the photo interrupter 5 formed by one light emitting element 52 and five light receiving elements 51, and the light emitting element 52 and the light receiving elements 51 are arranged at opposing or substantially opposing positions with the drip cylinder 11 interposed therebetween. The five light receiving elements 51 and the one light emitting element 52 are present on the same plane. The five light receiving elements 51 are aligned with the same orientation in a row in the longitudinal direction on the same plane. The light paths 53 connecting the light emitting element 52 to the light receiving elements 51 are located at the lower side relative to the lower end of the nozzle. In the disclosure, a positional relation between the light receiving elements and the light emitting element may be such relation that they are present on the same plane or such relation that they are present with different heights as long as they are arranged at opposing or substantially opposing positions with the drip cylinder interposed therebetween.

In the seventh embodiment, the drip cylinder 11 is arranged between the one light emitting element 52 and the five light receiving elements 51 at the side closer to the five light receiving elements 51.

As illustrated in FIG. 7, in the embodiment, a region sectioned by the light paths 53 connecting the one light emitting element 52 to the light receiving elements 51 at both ends among the five light receiving elements 51 and the cylinder inner surface of the drip cylinder 11 is a range R in the drip cylinder 11 in which the dripping of the liquid droplet 13 can be detected. It is therefore understood that as the drip cylinder 11 is arranged so as to be closer to the five light receiving elements 51, the area of the region is increased. That is to say, when the drip cylinder 11 is arranged at the side closer to the five light receiving elements 51, the range R in the drip cylinder 11 in which the dripping of the liquid droplet 13 can be detected is also increased. Therefore, the dripping of the liquid droplet 13 can be precisely detected even when the drip cylinder 11 is inclined.

Furthermore, the less number of light receiving elements 51 can cover a larger range in the drip cylinder 11 by arranging the drip cylinder 11 at the side closer to the light receiving elements 51. Accordingly, the position at which the drip cylinder 11 is arranged is preferably located between the light emitting element 52 and the light receiving elements 51 at the side closer to the light receiving elements 51.

Eighth Embodiment

In an eighth embodiment, another preferable position at which a drip cylinder configuring a dripping detection apparatus is arranged is described.

Figure 8:
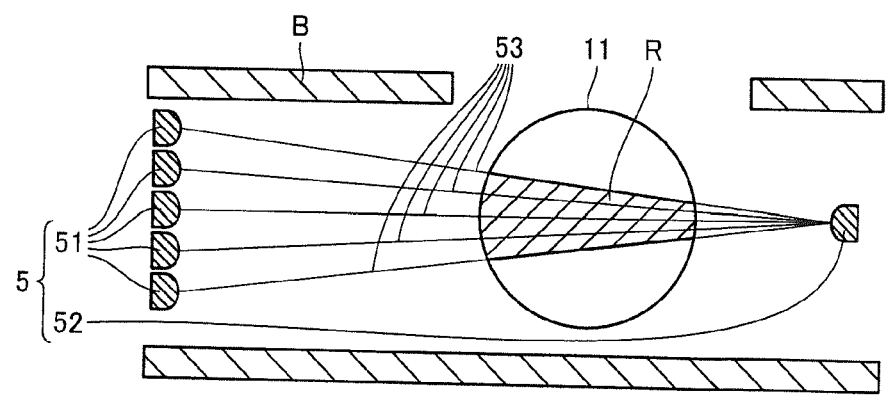
FIG. 8 is a partially cross-sectional descriptive view for schematically explaining an effect that is provided by a dripping detection apparatus according to an eighth embodiment.

The dripping detection apparatus in the eighth embodiment is different from the seventh embodiment in a point that the drip cylinder 11 is arranged between the one light emitting element 52 and the five light receiving elements 51 at the side closer to the one light emitting element 52, as illustrated in FIG. 8. Furthermore, a light shielding plate B preventing the disturbance light from being incident on the light receiving elements 51 is disposed and the light shielding plate B surrounds the drip cylinder 11, the light emitting element 52, and the light receiving elements 51. It should be noted that a gap is provided in a part of the light shielding plate B so as to enable a human or the like to visually check a part of the side surface of the drip cylinder 11.

In this configuration, it is understood that as a distance to the light receiving elements 51 from the gap provided in the light shielding plate B is larger, the disturbance light is more difficult to reach the light receiving elements 51 even when the disturbance light is incident from the gap. Therefore, in the embodiment, as the drip cylinder 11 is arranged at an extremely closer position to the one light emitting element 52, the distance to the light receiving elements 51 from the gap provided in the light shielding plate B is increased, thereby preventing the disturbance light from being incident on the light receiving elements 51. Accordingly, shadows of the liquid droplet 13 with high contrast can thereby be obtained in the light receiving elements 51, so that the dripping of the liquid droplet 13 can be detected more stably.

Moreover, the above-described configuration decreases the distances between the five light paths 53 connecting the five light receiving elements 51 to the one light emitting element 52 when seen from the above, thereby preventing the occurrence of the case in which the liquid droplet 13 passes through between one of the light path 53 and another one of the light paths 53. Accordingly, the position at which the drip cylinder 11 is arranged is also preferably located between the light emitting element 52 and the light receiving elements 51 at the side closer to the light emitting element 52.

Ninth Embodiment

Figure 9:
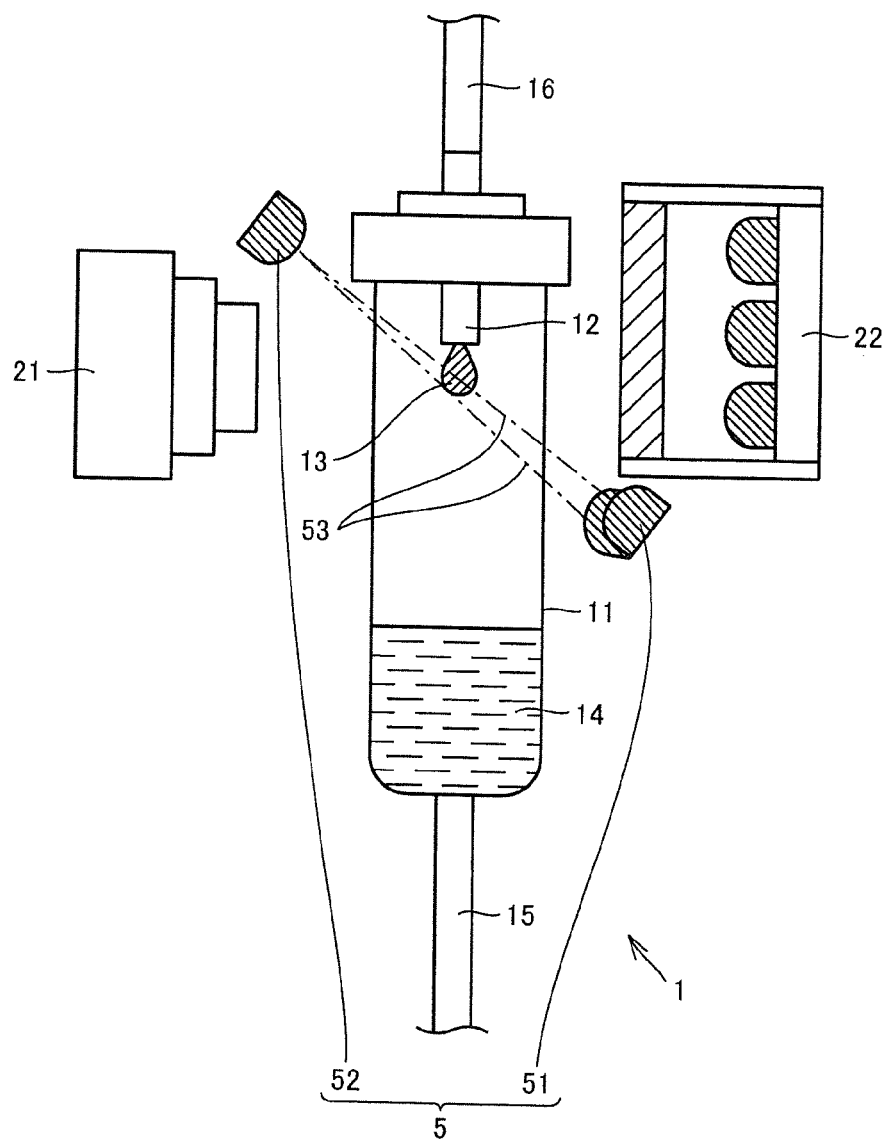
FIG. 9 is a schematic front view schematically illustrating the schematic configuration of a dripping detection apparatus according to a ninth embodiment.

The dripping detection apparatus 1 according to a ninth embodiment is different from the first embodiment in the following points. That is, the one light emitting element 52 and the three light receiving elements 51 aligned in a row in the depth direction are arranged at opposing or substantially opposing positions with the drip cylinder 11 interposed therebetween and at least one (three in the ninth embodiment) of three light paths 53 connecting the light emitting element 52 to the light receiving elements 51 intersects with the liquid droplet 13 growing on the lower end of the nozzle 12, as illustrated in FIG. 9. Furthermore, the dripping detection apparatus 1 in the ninth embodiment is different from the first embodiment in a point that the height of the light emitting element 52 when seen from the front side is different from the heights of the light receiving elements 51 when seen from the front side. To be specific, the height of the light emitting element 52 when seen from the front side is larger than the height of the light receiving elements 51 when seen from the front side.

In addition, the dripping detection apparatus 1 in the ninth embodiment is different from the first embodiment in a point that it includes an image capturing unit and an illumination unit. In the ninth embodiment, a camera 21 as the image capturing unit that shoots the liquid droplet 13 growing on the lower end of the nozzle 12 and an illumination device 22 as the illumination unit that is arranged at a position opposing or substantially opposing the camera 21 with the drip cylinder 11 interposed therebetween are included. Furthermore, the camera 21 and the light receiving elements 51 are arranged at opposing or substantially opposing positions with the drip cylinder 11 interposed therebetween.

In the embodiment, in particular, the one light emitting element 52 and the three light receiving elements 51 oppose respectively each other with the drip cylinder 11 interposed therebetween. The camera 21 and the respective light receiving elements 51 also oppose each other with the drip cylinder 11 interposed therebetween. The camera 21 and the illumination device 22 also oppose each other. In the disclosure, positions at which the light receiving elements and the light emitting element are arranged, positions at which the image capturing unit and the light receiving elements are arranged, and positions at which the image capturing unit and the illumination unit are arranged can be appropriately selected as long as they exert desired functions and are arranged at the opposing or substantially opposing positions with the drip cylinder interposed therebetween.

<Camera and Illumination Device>

The camera 21 (for example, two-dimensional image sensor) is arranged so as to be close to the side surface of the drip cylinder 11 such that an angle of view of the camera 21 contains a space in the vicinity of the lower end of the nozzle 12. In this state, the camera 21 can shoot the growing liquid droplet from the beginning of the growth on the lower end of the nozzle 12 to dropping at a plurality of time points and acquire a plurality of pieces of image data (for example, a series of moving image). The "growing" indicates a state during which the liquid droplet grows on the lower end of the nozzle, that is, during which the liquid droplet is gradually increased in size while the liquid droplet adheres to the lower end of the nozzle.

The illumination device 22 is provided at a position opposing the camera 21 with the drip cylinder 11 interposed therebetween. The illumination device 22 can illuminate at least the liquid droplet 13 growing on the lower end of the nozzle 12. The liquid droplet 13 can thereby be reliably shot by illumination even when the disturbance light is present. Furthermore, even when vibration or the like occurs, the shutter speed for one image can be increased by illumination, thereby providing images with less blur.

A stroboscope that repeatedly emits light at a constant interval can be used as the illumination device 22. The camera 21 has sensitivity to a wavelength of light that is emitted from the illumination device 22. For example, when the illumination device 22 is a surface-emitting infrared LED illumination, the camera 21 has sensitivity to a wavelength of infrared rays. When the infrared LED illumination is used, the light emitting element 22 is not dazzling even when a patient is subject to drip infusion in the nighttime or the like. Furthermore, the camera 21 may include an optical filter capable of cutting light with unnecessary wavelengths.

In the ninth embodiment, the liquid droplet 13 growing on the lower end of the nozzle 12 necessarily intersects with at least one (three in the ninth embodiment) of the three light paths 53 connecting the light emitting element 52 to the light receiving elements 51. Therefore, the light receiving elements 51 can necessarily detect the liquid droplet 13 even when the drip cylinder 11 is inclined with the motion of the patient, or the like. The occurrence of the dripping can be detected by detecting the absence of the liquid droplet 13 on the lower end of the nozzle 12.

Furthermore, the photo interrupter 5 is configured such that the height of the light emitting element 52 when seen from the front side is larger than the height of each of the light receiving elements 51 when seen from the front side and the light paths 53 connecting the light emitting element 52 to the light receiving elements 51 are inclined when seen from the front side. With this configuration, the camera 21 can be easily arranged such that the angle of view contains the space in the vicinity of the lower end of the nozzle 12 while the presence of the photo interrupter 5 is not an obstacle. Moreover, the illumination device 22 can be easily arranged at a position opposing the camera 21.

The camera 21 and the light receiving elements 51 are arranged at the opposing positions with the drip cylinder 11 interposed therebetween. With this arrangement, the illumination device 22 and the light receiving elements 51 are arranged at the same side. Therefore, the light emitted from the illumination device 22 can be prevented from being incident on the light receiving elements 51 as disturbance light.

In the embodiment, the volume of the liquid droplet 13 can be obtained by arranging the camera 21 such that the angle of view contains the space in the vicinity of the lower end of the nozzle 12 and shooting the liquid droplet 13 as a plurality of images or a moving image. Furthermore, the dripping rate (flow rate) can be obtained by specifying the number of times of dripping per unit time by the photo interrupter 5 and multiplying the number of times of dripping by the volume of the liquid droplet. Accordingly, with the embodiment, the dripping of the liquid droplet 13 can be precisely detected by the photo interrupter 5 formed by the light emitting element 52 and the light receiving elements 51 arranged as described above even when the drip cylinder 11 is inclined with the motion of the patient, or the like. In addition, the camera 21 and the illumination device 22 can be easily added and the dripping rate can be accurately measured using the volume of the liquid droplet 13, which can be calculated using the camera 21 and the illumination device 22, regardless of the types of the liquid droplet.

Although in the above-described ninth embodiment, the photo interrupter 5 is configured by the one light emitting element 52 and the three light receiving elements 51 as an example, the disclosure is not limited to this configuration. The photo interrupter can be configured by equal to or more than one light emitting element and equal to or more than two light receiving elements as long as they are arranged at the opposing or substantially opposing positions with the drip cylinder interposed therebetween and at least one of equal to or more than two light paths intersects with the liquid droplet growing on the lower end of the nozzle. The number of light emitting elements and the number of light receiving elements may be the same as or different from each other as long as the photo interrupter is configured by equal to or more than one light emitting element and equal to or more than two light receiving elements.

Tenth Embodiment

The dripping detection apparatus 1 according to a tenth embodiment is different from the first embodiment in the following points. That is, the one light emitting element 52 and the three light receiving elements 51 aligned in a row in the depth direction are arranged at the opposing or substantially opposing positions with the drip cylinder 11 interposed therebetween and at least one (one in the tenth embodiment) of the three light paths 53 connecting the light emitting element 52 to the light receiving elements 51 is used for detecting a liquid level of the liquid reservoir 14 in the drip cylinder 11, as illustrated in FIG. 10.

Figure 10:
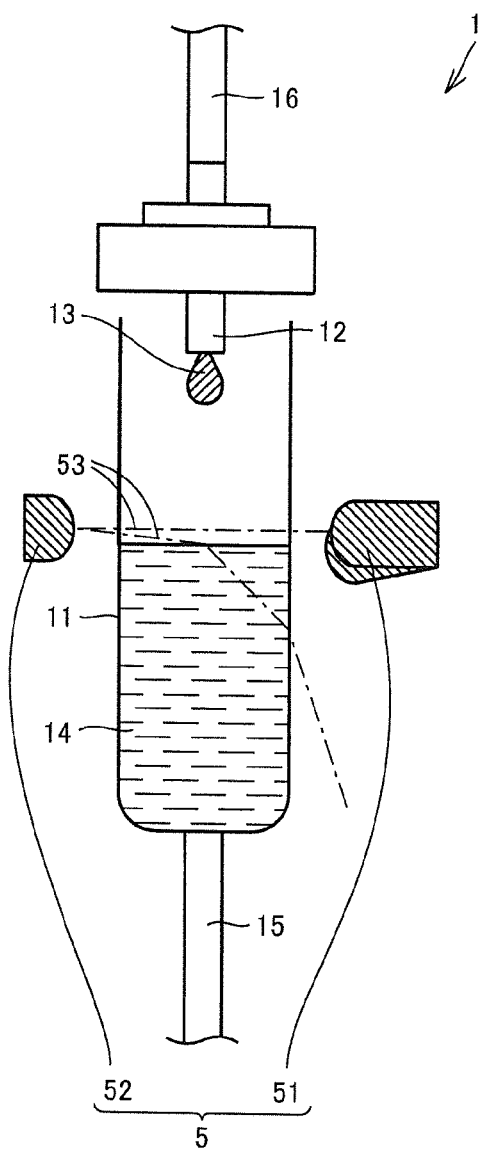
FIG. 10 is a schematic front view schematically illustrating the schematic configuration of a dripping detection apparatus according to a tenth embodiment.

That is to say, as illustrated in FIG. 10, in the dripping detection apparatus 1 in the tenth embodiment, in a state in which the liquid level of the liquid reservoir 14 in the drip cylinder 11 has reached the light paths 53 or in a state immediately before the liquid level reaches the light paths 53, one of the three light paths 53 connecting the light emitting element 52 to the light receiving elements 51 is refracted by the liquid surface of the liquid reservoir 14. The light receiving portion of the one light receiving element 51 for detecting the liquid level of the liquid reservoir 14 therefore detects that light from the light emitting element 52 does not reach it (that is, is shielded) over a predetermined period of time or through a predetermined period of time or the light amount of light from the light emitting element 52 has varied. The light receiving portion of the light receiving element 51 recognizes the above-described detection as abnormal in the liquid level of the liquid reservoir 14. Thus, the light path 53 can be made to have a function as a liquid level sensor of the liquid reservoir 14.

Although also in the tenth embodiment, the photo interrupter 5 is configured by the one light emitting element 52 and the three light receiving elements 51 as an example, the disclosure is not limited to this configuration. The photo interrupter can be configured by equal to or more than one light emitting element and equal to or more than two light receiving elements as long as they are arranged at the opposing or substantially opposing positions with the drip cylinder interposed therebetween and at least one of the equal to or more than two light paths is used for detecting the liquid level of the liquid reservoir in the drip cylinder. The number of light emitting elements and the number of light receiving elements may be the same as or different from each other as long as the photo interrupter is configured by equal to or more than one light emitting element and equal to or more than two light receiving elements.

Eleventh Embodiment

Figure 11:
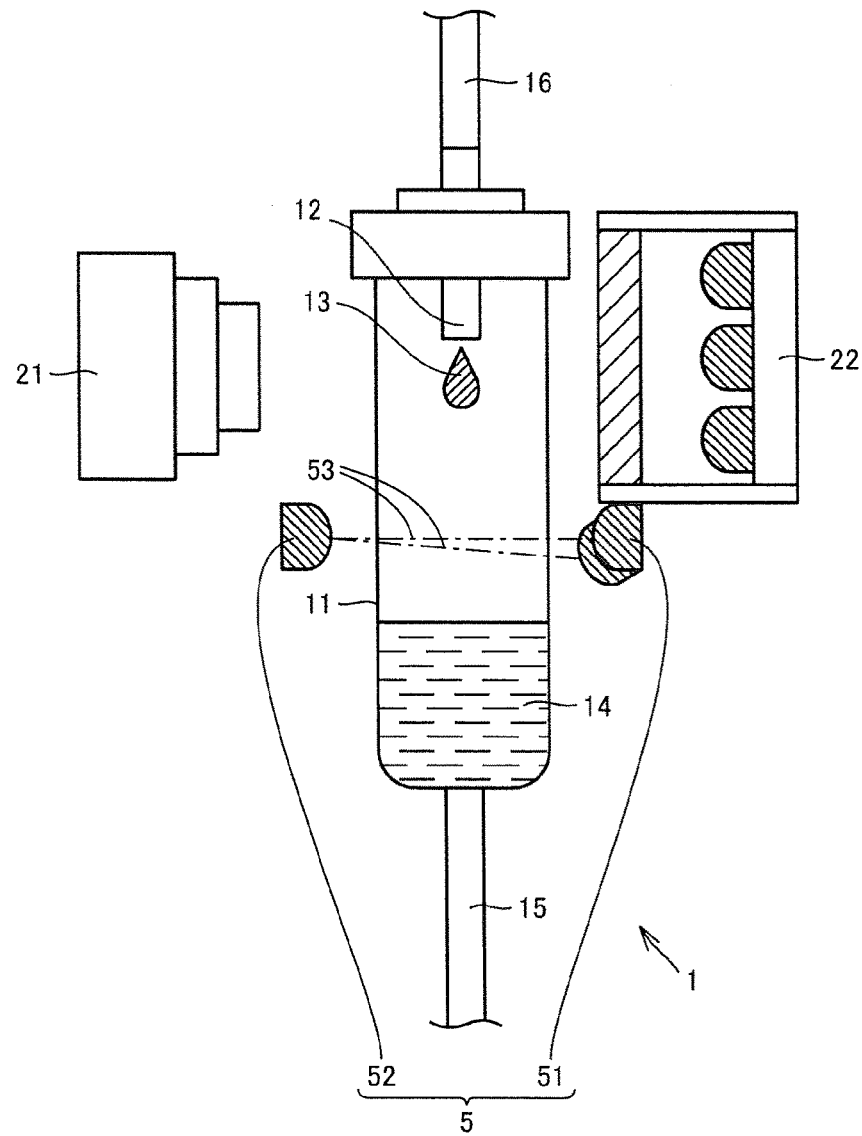
FIG. 11 is a schematic front view schematically illustrating the schematic configuration of a dripping detection apparatus according to an eleventh embodiment.

A dripping detection apparatus according to an eleventh embodiment is different from the ninth embodiment in a point that equal to or more than one light emitting element 52 and equal to or more than two light receiving elements 51 (three light receiving elements 51 are aligned in a row in the depth direction in FIG. 11) are arranged at opposing or substantially opposing positions with the drip cylinder 11 interposed therebetween at the lower side relative to the lower end of the nozzle 12, as illustrated in FIG. 11. In addition, in the eleventh embodiment, the camera 21 that shoots the liquid droplet 13 growing on the lower end of the nozzle 12 and the illumination device 22 that is arranged at the position opposing or substantially opposing the camera 21 with the drip cylinder 11 interposed therebetween are included in the same manner as the ninth embodiment.

In the embodiment, the photo interrupter 5 that is configured by the light emitting elements 52 and the light receiving elements 51 as described in any of the first embodiment to the eighth embodiment can be used. With the usage of the photo interrupter 5, the light receiving elements 51 can necessarily detect the liquid droplet 13 even when the drip cylinder 11 is inclined with the motion of the patient, or the like. Furthermore, the camera 21 and the light receiving elements 51 are preferably arranged at the opposing or substantially opposing positions with the drip cylinder 11 interposed therebetween, as illustrated in FIG. 11. With this arrangement, the illumination device 22 and the light receiving elements 51 are arranged at the same side. Therefore, the light emitted from the illumination device 22 can be prevented from being incident on the light receiving elements 51 as disturbance light.

Moreover, in the embodiment, the camera 21 and the illumination device 22 can be easily added regardless of the presence of the photo interrupter 5 and the dripping rate can be accurately measured using the volume of the liquid droplet 13, which can be calculated using the camera 21 and the illumination device 22, regardless of the types of the liquid droplet.

Twelfth Embodiment

Figure 12:
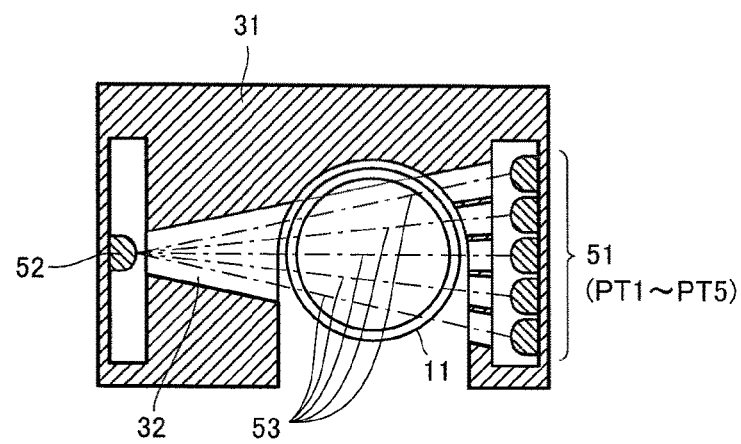
FIG. 12 is a schematic plan view schematically illustrating the schematic configuration of a dripping detection apparatus according to a twelfth embodiment in a state in which a nozzle has been detached while omitting the illustration of a liquid reservoir.
Figure 13:
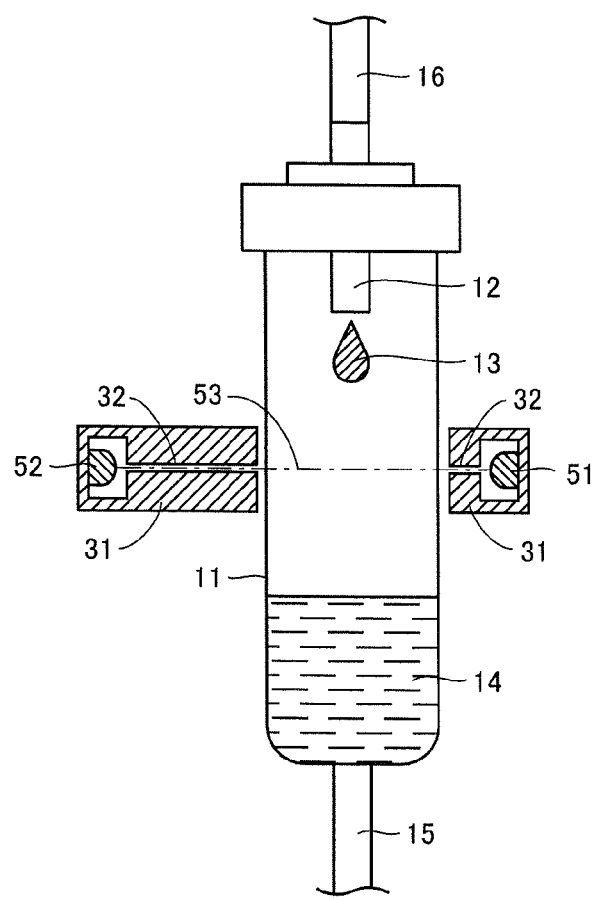
FIG. 13 is a partially cross-sectional view of a schematic front side, which schematically illustrates the schematic configuration of the dripping detection apparatus in the twelfth embodiment.

The dripping detection apparatus 1 according to a twelfth embodiment is different from the first embodiment in a point that it includes a housing 31. The housing 31 accommodates therein a part of the drip cylinder 11, the light emitting element 52, and the light receiving elements 51, as illustrated in FIG. 12 and FIG. 13. The dripping detection apparatus 1 in the twelfth embodiment is different from the first embodiment also in a point that five light receiving elements 51 are aligned in a row in the depth direction. Other configurations can be made the same as those in the first embodiment.

That is to say, the dripping detection apparatus 1 in the twelfth embodiment is configured such that the light receiving elements 51, the light emitting element 52, and a part of the drip cylinder 11 are accommodated in the housing 31, as illustrated in FIG. 12 and FIG. 13. A fine hole 32 is formed in the housing 31. The fine hole 32 is a hole through which the light paths 53 connecting the light emitting element 52 to the light receiving elements 51 pass. Accordingly, in the dripping detection apparatus 1 in the twelfth embodiment, the light emitting element 52 and the five light receiving elements 51 are arranged such that the light paths 53 connecting the light emitting element 52 to the five light receiving elements 51 pass through the fine hole 32. The light paths 53 are not therefore blocked by the housing 31.

The housing 31 has a function of blocking the influences by the disturbance light incident from the outside of the dripping detection apparatus 1, such as sunlight, like the light shielding plate B in the dripping detection apparatus in the above-described eighth embodiment. The housing 31 can contribute more accurate detection of the dripping of the liquid droplet by the photo interrupter 5. A material of the housing 31 is not limited as long as the influences by the incidence of the above-described disturbance light can be blocked. Furthermore, a gap is preferably provided in a part of the housing 31 so as to enable a human or the like to visually check a part of the side surface of the drip cylinder 11.

Thirteenth Embodiment

Figure 14:
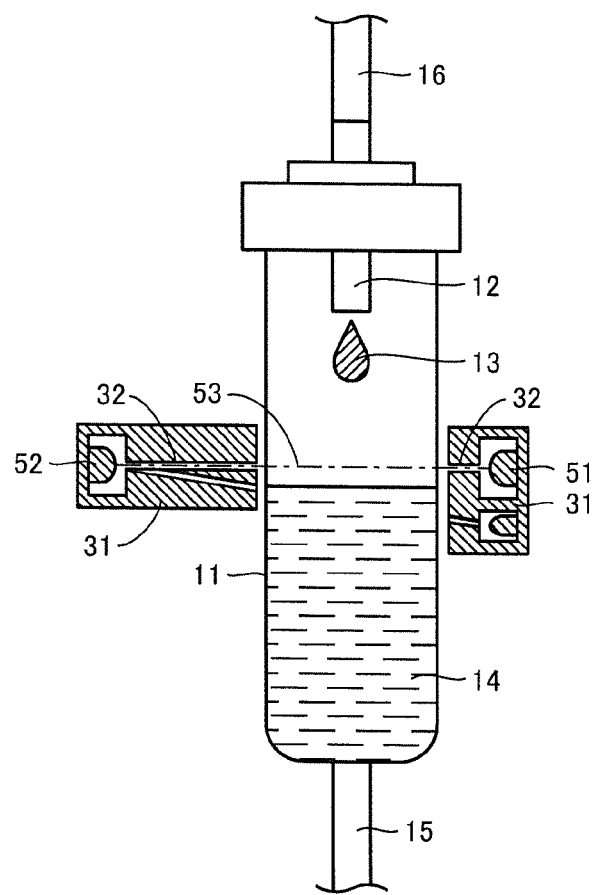
FIG. 14 is a partially cross-sectional view of a schematic front side, which schematically illustrates the schematic configuration of a dripping detection apparatus according to a thirteenth embodiment.

The dripping detection apparatus 1 according to a thirteenth embodiment is different from the eleventh embodiment in the following point. That is, the housing 31 accommodates therein one light emitting element 52 and six light receiving elements 51 including one light receiving element 51 for detecting the liquid level of the liquid reservoir 14 like the dripping detection apparatus 1 in the twelfth embodiment, as illustrated in FIG. 14. The fine hole 32 through which the light paths 53 connecting the light emitting element 52 to the light receiving elements 51 pass is also formed in the housing 31.

The dripping detection apparatus 1 in the thirteenth embodiment can have a function of blocking the influences by the disturbance light incident from the outside of the dripping detection apparatus 1, such as sunlight, by including the above-described housing 31 in the same manner as the twelfth embodiment. As illustrated in FIGS. 15A, 15B and 15C, the photo interrupter 5 can detect the dripping of the liquid droplet more accurately and can detect the generation of abnormality for the liquid level of the liquid reservoir 14 more accurately. For example, FIGS. 15A, 15B and 15C illustrate respective examples in which the photo interrupter 5 detects the liquid level of the liquid reservoir 14 to be a high level, a middle level, and a low level. The light receiving elements 51 detecting the dripping of the liquid droplet and the light receiving element 51 for detecting the liquid level are preferably arranged with a constant distance therebetween. The arrangement manner can prevent the liquid receiving element 51 for detecting the liquid level from mistakenly detecting a liquid droplet splashed back from the liquid surface as abnormal in the liquid level when the liquid droplet drips into the liquid reservoir 14 in the drip cylinder 11. A material of the housing 31 is not limited as long as the above-described influences by the incidence of the disturbance light can be blocked in the same manner as the twelfth embodiment. A gap is also preferably provided in a part of the housing 31 so as to enable a human or the like to visually check a part of the side surface of the drip cylinder 11.

Figure 16A:
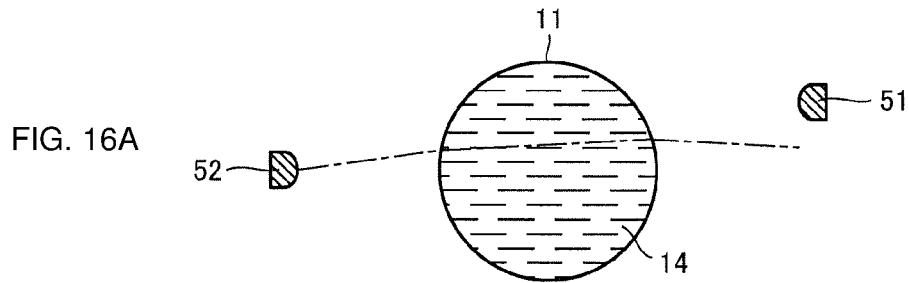
FIGS. 16A and 16B are descriptive views for schematically explaining the effect that is provided by the dripping detection apparatus in the thirteenth embodiment when seen from the above.
Figure 16B:
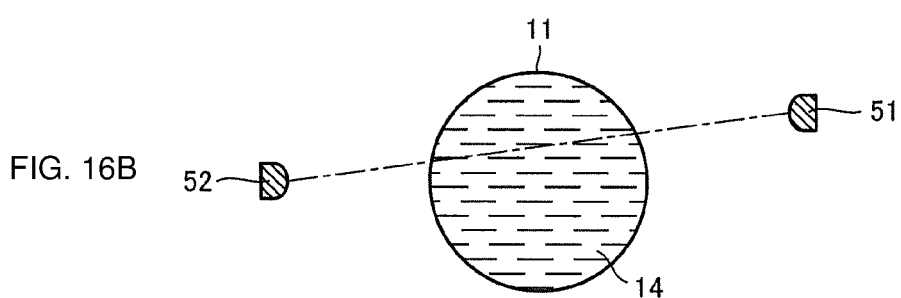

In FIGS. 15A, 15B and 15C, variations of the light paths 53 appear only in the up-down direction when the photo interrupter 5 detects the liquid level of the liquid reservoir 14 because FIGS. 15A, 15B and 15C are front views. Therefore, when the liquid level of the liquid reservoir 14 is the high level in the dripping detection apparatus 1 illustrated in FIG. 15A, it is grasped that light from the light emitting element 52 seems to be incident on the light receiving element 51 for detecting the liquid level. However, as illustrated in the descriptive view when seen from the above in FIG. 16A, when the liquid level of the liquid reservoir 14 is the high level in the dripping detection apparatus 1 in the embodiment, the light from the light emitting element 52 is not incident on the light receiving element 51 for detecting the liquid level because the light path 53 thereof is refracted to the planar direction by the liquid reservoir 14. Accordingly, the dripping detection apparatus 1 in the embodiment can also detect the abnormality of the liquid level even when the liquid level of the liquid reservoir 14 is the high level in the same manner as the case in which the liquid level is the middle level. FIG. 16B also illustrates the dripping detection apparatus 1 when the liquid level of the liquid reservoir 14 is the low level (illustrates it in a lower portion). In this case, the light from the light emitting element 52 is incident on the light receiving element 51 for detecting the liquid level while the light path 53 thereof is not refracted by the liquid reservoir 14.

For example, a preferable circuit configuration when the three light receiving elements are arranged in the dripping detection apparatus in the disclosure will be described with reference to FIG. 17A to FIG. 17C.

Figure 17A:
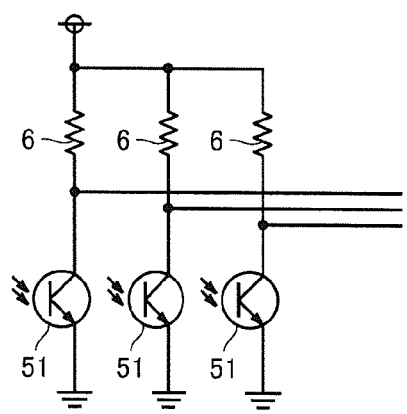
FIG. 17A is a descriptive view related to a circuit configuration of a dripping detection apparatus according to the disclosure for explaining an example in which light receiving elements and resistors are connected in series.
Figure 17B:
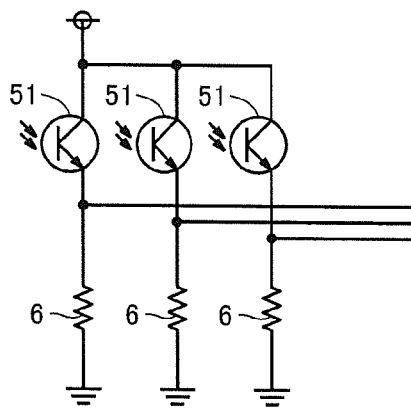
FIG. 17B is a descriptive view related to the circuit configuration of the dripping detection apparatus in the disclosure for explaining another example in which the light receiving elements and the resistors are connected in series.

For example, as illustrated in FIG. 17A and FIG. 17B, the circuit configuration in which resistors 6 are connected in series to the respective light receiving elements 51 and potentials between the light receiving elements 51 and the resistors 6 are respectively detected is employed. In this case, the light receiving portions of the respective light receiving elements 51 can independently grasp whether or not the light emitted from the light emitting element 52 is shielded by the dripping liquid droplet 13. Therefore, the dripping of the liquid droplet 13 can be detected extremely precisely and the circuit configuration is advantageous.

Figure 17C:
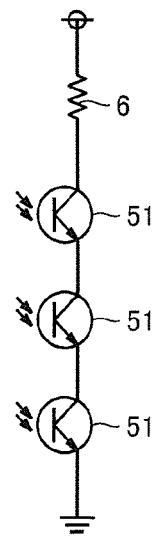
FIG. 17C is a descriptive view related to the circuit configuration of the dripping detection apparatus in the disclosure for explaining an example in which all of the light receiving elements are connected in series and the resistor is further connected thereto in series.

Alternatively, as illustrated in FIG. 17C, the circuit configuration in which all of the three light receiving elements 51 are connected in series and are further connected in series to the resistor 6, and variation in the potential, which shows the decrease in a flowing current, is detected is employed. In this case, the light receiving portion of at least any of the light receiving elements 51 can detect the above-described variation in the potential by grasping whether or not the light emitted from the light emitting element 52 is shielded by the dripping liquid droplet 13. Therefore, even this circuit configuration enables dripping of the liquid droplet 13 to be detected extremely precisely and is advantageous.

Alternatively, when the plurality of light emitting elements 52 and the plurality of light receiving elements 51 are arranged, the light emitting elements 52 are made to emit light in order in a time-division manner, and the light receiving elements 51 opposing or substantially opposing the light elements 52 with the drip cylinder 11 interposed therebetween detect the occurrence of the light shielding by the liquid droplet 13 in order so as to correspond to the light emission. For example, in the above-described fourth embodiment and fifth embodiment in which the three light emitting elements 52 and the three light receiving elements 51 oppose each other, the three light emitting elements 52 are made to emit light in order at a frequency of several ten kHz, for example, and the corresponding light receiving elements 51 grasp in order whether or not the emitted light is shielded by the dripping liquid droplet 13. Also in this case, the dripping of the liquid droplet 13 can be detected extremely precisely.

The light receiving portions of the light receiving elements can detect the dripping of the liquid droplet precisely even with the configuration in which they grasp the variation in the light amount based on the passage of the light emitted from the light emitting element through the dripping liquid droplet, as described above.

Although some embodiments have been described above as examples of the disclosure, it is also expected that the configurations in the above-described respective embodiments are appropriately combined or variously modified.

It should be considered that the embodiments disclosed herein are exemplary and are non-limiting in all the points. The scope of the present disclosure is defined not by the above description but by the scope of the disclosure and encompasses all changes within equivalent meanings and ranges to those of the scope of the disclosure.

1 DRIPPING DETECTION APPARATUS
11 DRIP CYLINDER
12 NOZZLE
13 LIQUID DROPLET
14 LIQUID RESERVOIR
15 TUBE
16 TUBE
21 CAMERA (IMAGE CAPTURING UNIT)
22 ILLUMINATION DEVICE (ILLUMINATION UNIT)
31 HOUSING
32 FINE HOLE
5 PHOTO INTERRUPTER
51 LIGHT RECEIVING ELEMENT
52 LIGHT EMITTING ELEMENT
53 LIGHT PATH
6 RESISTOR
R RANGE IN DRIP CYLINDER IN WHICH DRIPPING OF LIQUID DROPLET CAN BE DETECTED.

The invention claimed is:

1. A dripping detection apparatus comprising:
a cylindrical drip cylinder having a nozzle inserted from an upper side of the cylindrical drip cylinder, and receiving a liquid droplet dripping from a lower end of the nozzle inside the cylindrical drip cylinder;
a photo interrupter having one or more light emitting elements configured to emit light, and two or more light receiving elements configured to receive the light; and
a controller and/or an analog circuit,
wherein the one or more light emitting elements and the two or more light receiving elements are arranged at opposing or substantially opposing positions of the cylindrical drip cylinder, thereby forming two or more light paths connecting the one or more light emitting elements and corresponding light receiving elements,
wherein the light paths are located at a lower side relative to the lower end of the nozzle,
wherein a height of a first light path of the two or more light paths is different from a height of a second light path of the two or more light paths, the heights being measured from a bottom of the cylindrical drip cylinder,
wherein a number of light receiving elements is equal to a number of light paths, each light receiving element corresponding to a different one of the two or more light paths,
wherein the number of light receiving elements is greater than a number of light emitting elements,
wherein the first light path is not parallel with the second light path, and
wherein the controller and/or the analog circuit is configured to measure a number of drips based at least in part on light received from the first light path, and to measure a liquid level of a liquid reservoir in the cylindrical drip cylinder based at least in part on light received from the second light path.

2. The dripping detection apparatus according to claim 1, wherein at least one of the two or more light paths is non-parallel with another one of the two or more light paths when seen from above.

3. The dripping detection apparatus according to claim 1, wherein at least one of the two or more light paths is non-parallel with another one of the two or more light paths when seen from a front side.

4. The dripping detection apparatus according to claim 1, wherein the cylindrical drip cylinder is arranged between the light emitting element and the two or more light receiving elements at a location closer to the two or more light receiving elements.

5. The dripping detection apparatus according to of claim 1, wherein at least one of the two or more light paths intersects with the liquid droplet growing on the lower end of the nozzle.

6. The dripping detection apparatus according to claim 1, further comprising:
an image capturing unit configured to capture the liquid droplet growing on the lower end of the nozzle; and
an illumination unit arranged at a position opposing or substantially opposing the image capturing unit with the cylindrical drip cylinder between the illumination unit and the image capturing unit,
wherein the image capturing unit and the two or more light receiving elements are arranged at opposing or substantially opposing positions of the cylindrical drip cylinder interposed between the image capturing unit and the two or more light receiving elements.

7. The dripping detection apparatus according to claim 2, wherein at least one of the two or more light paths is non-parallel with another one of the two or more light paths when seen from a front side.

8. The dripping detection apparatus according to of claim 2, wherein at least one of the two or more light paths intersects with the liquid droplet growing on the lower end of the nozzle.

9. The dripping detection apparatus according to of claim 3, wherein at least one of the two or more light paths intersects with the liquid droplet growing on the lower end of the nozzle.

10. The dripping detection apparatus according to of claim 1, wherein at least one of the two or more light paths intersects with the liquid droplet growing on the lower end of the nozzle.

11. The dripping detection apparatus according to of claim 4, wherein at least one of the two or more light paths intersects with the liquid droplet growing on the lower end of the nozzle.

* * * * *